(12) United States Patent
Nielsen et al.

(10) Patent No.: US 8,878,677 B2
(45) Date of Patent: Nov. 4, 2014

(54) SYSTEM AND METHOD FOR AUTOMATIC CAPTURE AND ARCHIVE OF CLINICALLY MEANINGFUL VITALS

(75) Inventors: Larry Nielsen, Burlington, MA (US); Gregory H. Raber, Sterling, MA (US); Brian D. Gross, North Andover, MA (US); Wei Zong, Belmont, MA (US); Mohammed Saeed, Cambridge, MA (US)

(73) Assignee: Koninklijke Philips N.V., Eindhoven (NL)

( * ) Notice: Subject to any disclaimer, the term of this patent is extended or adjusted under 35 U.S.C. 154(b) by 269 days.

(21) Appl. No.: 13/147,373

(22) PCT Filed: Jan. 12, 2010

(86) PCT No.: PCT/IB2010/050109
§ 371 (c)(1),
(2), (4) Date: Aug. 2, 2011

(87) PCT Pub. No.: WO2010/095064
PCT Pub. Date: Aug. 26, 2010

(65) Prior Publication Data
US 2011/0316704 A1     Dec. 29, 2011

Related U.S. Application Data

(60) Provisional application No. 61/152,979, filed on Feb. 17, 2009.

(51) Int. Cl.
*G08B 23/00*     (2006.01)
*G06F 19/00*     (2011.01)
*G06F 17/40*     (2006.01)
*A61B 5/00*      (2006.01)
*A61B 5/021*     (2006.01)
*A61B 5/0205*    (2006.01)

(52) U.S. Cl.
CPC ............ *A61B 5/0002* (2013.01); *A61B 5/7232* (2013.01); *A61B 5/021* (2013.01); *A61B 5/0205* (2013.01); *A61B 5/7221* (2013.01); *G06F 19/3487* (2013.01); *A61B 5/7203* (2013.01); *G06F 19/345* (2013.01)
USPC ......... 340/573.1; 600/300; 600/546; 600/549

(58) Field of Classification Search
USPC ....................................... 340/573.1; 128/905
See application file for complete search history.

(56) References Cited

U.S. PATENT DOCUMENTS 5,190,038 A  *  3/1993  Polson et al. ................. 600/330
5,810,740 A      9/1998  Paisner
6,358,213 B1 *  3/2002  Friedman et al. ............ 600/493

(Continued)

FOREIGN PATENT DOCUMENTS

EP           1077042 A1     2/2001
JP           10165377 A     6/1998

OTHER PUBLICATIONS

Aboukhalil, A., et al.; Reducing false alarm rates for critical arrhythmias using the arterial blood pressure waveform; 2008; Journal of Biomedical Informatics; 41:442-451.

*Primary Examiner* — Brian Zimmerman
*Assistant Examiner* — Bhavin M Patel

(57) ABSTRACT

Medical vital signs (110) are captured, recorded, processed, and a signal quality assessment (160) is computed based on signal waveform components such as slope, amplitude, time to rise, time at peak, and degree to which signal peaks (420) and valleys (430). The signal assessment (160) may be used as a basis for rating the quality (130) of the underlying vital signal, to increase the quality of the signal by removing noisy segments and physiologically impossible peaks (42) and valleys (434), to detect a parameter value (120), to label a waveform (140), or to prompt an alarm (550) to indicate the signal has reached a critical level and issue a warning to the user of the vital data. The signal and the assessment are stored in an indexed, searchable data storage memory (590) from which the signals may be retrieved and displayed (300).

20 Claims, 7 Drawing Sheets

(56) References Cited

U.S. PATENT DOCUMENTS

| | | |
|---|---|---|
| 2004/0138540 A1 | 7/2004 | Baker, Jr. et al. |
| 2006/0030764 A1 | 2/2006 | Porges et al. |
| 2006/0135860 A1 | 6/2006 | Baker, Jr. et al. |
| 2006/0200009 A1 | 9/2006 | Wekell et al. |
| 2007/0239220 A1 | 10/2007 | Greenhut et al. |
| 2008/0139898 A1* | 6/2008 | Johnson et al. ............... 600/301 |
| 2008/0183050 A1 | 7/2008 | Kontothanassis et al. |
| 2008/0183847 A1 | 7/2008 | Kontothanassis et al. |

* cited by examiner

SYSTEM AND METHOD FOR AUTOMATIC CAPTURE AND ARCHIVE OF CLINICALLY MEANINGFUL VITALS

CROSS REFERENCE TO RELATED APPLICATIONS

This application claims the benefit of U.S. provisional application Ser. No. 61/152,979 filed Feb. 17, 2009, which is incorporated herein by reference.

The present application relates to the art of data collection and storage. It finds particular application to the collection of medical vital signs data and will be described with particular reference thereto. However, it will also find application in other types of displays.

Vital signs, or signs of life, include the following key objective clinical measurements: temperature, respiratory rate, heart rate, blood pressure and, where appropriate, blood oxygen saturation. These numbers provide critical vital information about a patient's state of health. All of these vital signs can be observed, measured, and monitored. Their measurement enables the assessment of the level at which an individual is functioning.

In particular, vital signs may indicate that a person is alive, identify the existence of an acute medical problem, be a means for rapidly quantifying the magnitude of an illness and how well the body is coping with the resultant physiologic stress, and may act as a marker of chronic disease states such as hypertension defined as chronically elevated blood pressure.

The benefits provided by automatic data collection of temperature, respiratory rate, heart rate, invasive/non-invasive blood pressure, or oxygen saturation from acute care monitoring devices have become so obvious that hospitals now require that their clinical information system (CIS), anesthesia information management system (AIMS), electronic medical records (EMR), electronic patient record system (EPR), or other hospital/healthcare information system (HIS) provide interfacing capabilities to biomedical devices in order to ensure that key vital signs are stored in the Centralized Data Repository (CDR) and to track patient progress over time.

While the importance of measuring, monitoring, observing and collecting clinical vital signs is not questioned, the accuracy and reliability of these measured vital signs may be questioned by medical practitioner users. A problem with vital signs manually collected from the acute care monitors, or from a nurse validated vital sign in CIS are that such vital signs are representative of the vital signs at that moment in time. Such measurements are point abstractions which do not capture the most physiologically meaningful values such as peaks, valleys, and pathway travelled by that vital sign since it was last measured, monitored, observed and collected. Another problem with systems that try to capture the peaks and valleys is that they capture the highs and lows of the acute care monitor including the errors from signal noise and artifacts as well as signal dropouts. Filtering of this signal, or excluding extremes may reduce the errors, but does not remove such errors. Another problem with such results is that they do not produce a record of the extremes to validate the accuracy and reliability of such measurements. Because of such problems, the diagnosis or interpretation of the data becomes ambiguous or misleading, the alarm performance appears to be poor, and clinical inference engines or advisories frequently become ineffective. A further problem is that clinical users remain suspicious of automatically charted vital sign data because of the shortcomings of automated algorithms to distinguish noise from physiologic changes.

The present application presents a system that stores trended vital signs, and also produces associated waveforms in order to allow a user to interrogate the data to observe, recalculate, or verify a vital sign.

The present application introduces an automated signal quality assessment and control mechanism into patient monitoring CIS for automatic capturing vital sign values associated with good, clean physiological signals. Un-trustful or unreliable measurements associated with noise, artifacts and equipment problems are automatically detected and excluded from entering in the CIS inference engine for diagnosis and decision making purposes. Physiologically meaningful values and trends can be automatically captured, the vital alarm performance can be significantly improved, and the clinical inference engines/advisories can be much more effective and trustful.

The present application provides an improved system and method of capturing, storing, and graphically presenting vitals data. The present application is based on a new understanding and insight. It utilizes a new signal quality indicator from one or more physiologic waveform signals upon which the vital signs are derived to automatically capture accurate and reliable derived vital signs and associated raw waveform snippets that are representative clinical meaningful attributes of clinical data.

In accordance with one aspect, a signal processing system is presented which is comprised of at least one Signal Quality Assessment (SQA)-equipped processing unit; an information processor; a searchable data storage medium; and a selectable data display medium.

In accordance with one aspect, a signal quality assessment and control system is presented for capturing and archiving physiologically meaningful monitored data comprising a parameter value detection processing unit which receives raw physiological parameter signals (in which there may be untrustful or unreliable portions) and generates physiologically meaningful and reliable parameter data, a signal quality assessment processing unit which receives the physiological signals, accesses quality of the physiological signals, and generates signal quality indices indicative of the assessed quality of the physiological signals, and a waveform labeling unit which associates the signal quality indices with the physiological waveform data.

In accordance with one aspect, a method is presented for capturing and archiving a signal quality assessment and control by creating a signal quality indicator comprising the steps of capturing the peak, the valley, and the raw signal of physiological parameter signals, generating physiological parameter data through a parameter value detection processing unit to provide auto-charted data to the electronic record, by sampling and saving occasional waveform snippets, sampling and saving featured vectors, and compressing the waveform snippets and vector features to record patient encounter recovery, receiving physiological parameter signals, accesses quality of the physiological parameter signals, and generates a signal quality index indicative of the assessed quality of the physiological parameter signal through a signal quality assessment processing unit, and associating the signal quality indices with the physiological parameter data at a waveform labeling unit and archiving the patient encounter history in a computer operable database.

In accordance with one aspect, a method is presented of compressing the medical vital sign history of a patient encounter is presented which is comprised of receiving a vital sign; creating a signal quality indicator (SQI), capturing peak, valley, and vitals of a vital sign through using the SQI, producing a high-quality vital sign by removing the physiologically impossible or technically untrustful peaks and valleys from the vital signal, storing a high quality vital sign, and displaying the high-quality vital sign.

In accordance with one aspect, a signal processing system is presented which comprises at least one SQA-equipped processing unit comprising a parametric value detection component, a signal quality assessment component, and a waveform label component; an Information Central Station (ICS) processor comprising a data-capture control (DCC), a system-level alarm manager, a clinical decision support (CDS) engine/clinical advisory, an event-evidence review control, a computer operable data storage memory containing an indexed searchable data set; and a selectable data display medium consisting of at least one of a computer display monitor, a waveform monitor, and an LED display.

An advantage resides in the creation of an SQI for a vital sign reflective of the accuracy and reliability of the measurement at that moment in time.

A further advantage is the utilization of the SQI's to improve quality and reliability of vital trends.

Another advantage is utilization of the SQI's to capture peak and valley of vitals along with associated raw signal snippets that do not include faulty extremes caused by noise and signal dropouts.

A still further advantage resides in an automatic capture of physiologically meaningful peaks, valleys, and typical vitals.

An advantage resides in a method to provide high quality "auto-charted" data to the Electronic Medical Record (EMR).

A still further advantage resides in a method to automatically reduce or compress the history of the patient encounter.

The present application would be useful to all clinicians in all areas of the hospital, from the lowest acuity to the highest acuity patients. Another use would be for the higher acuity patients that are having multiple measurements performed at the same time. It would be useful at the point of care as well as central and remote. Thus, it would find application on all bedside monitors as well as central stations, clinical information systems and/or hospital information systems.

The present application may take form in various components and arrangements of components, and in various steps and arrangements of steps. The drawings are only for purposes of illustrating the preferred embodiments and are not to be construed as limiting the present application.

Figure 3:
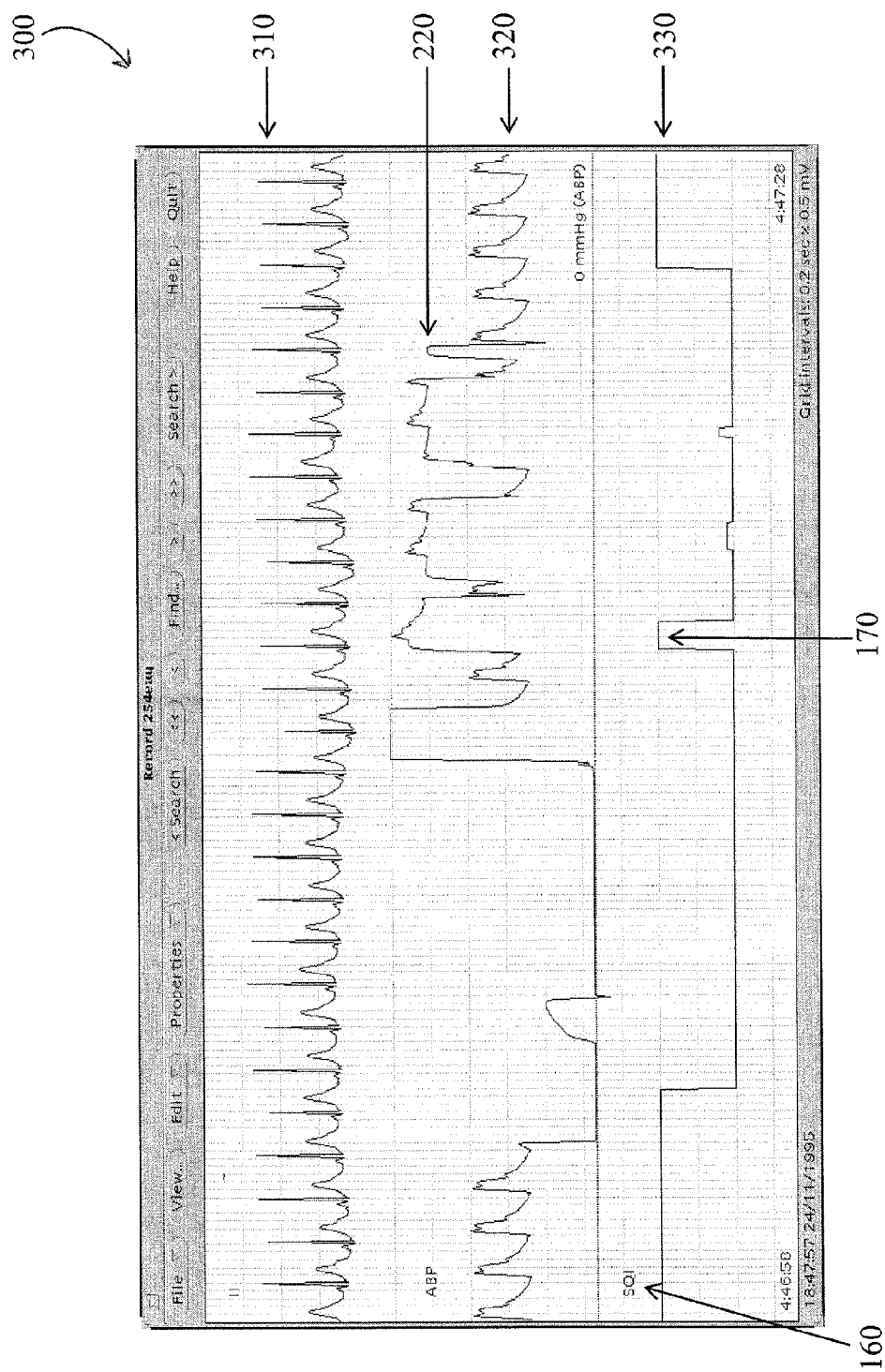

FIG. 3 presents an example of an ABP signal quality index.

Figure 4:
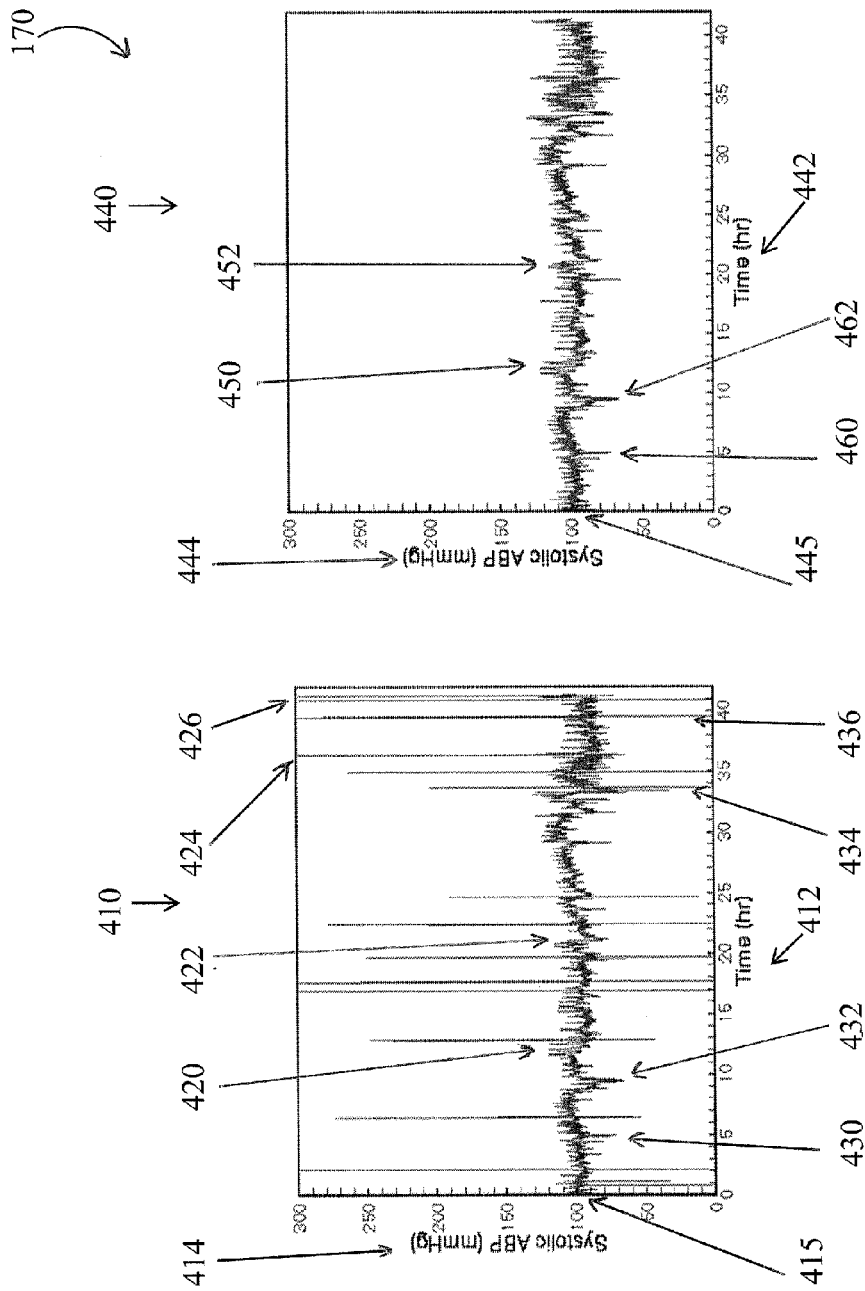

FIG. 4A presents an example of ABP readings over 40 hours without SQA and control.

FIG. 4B presents an example of ABP readings with SQA and control.

Figure 5:
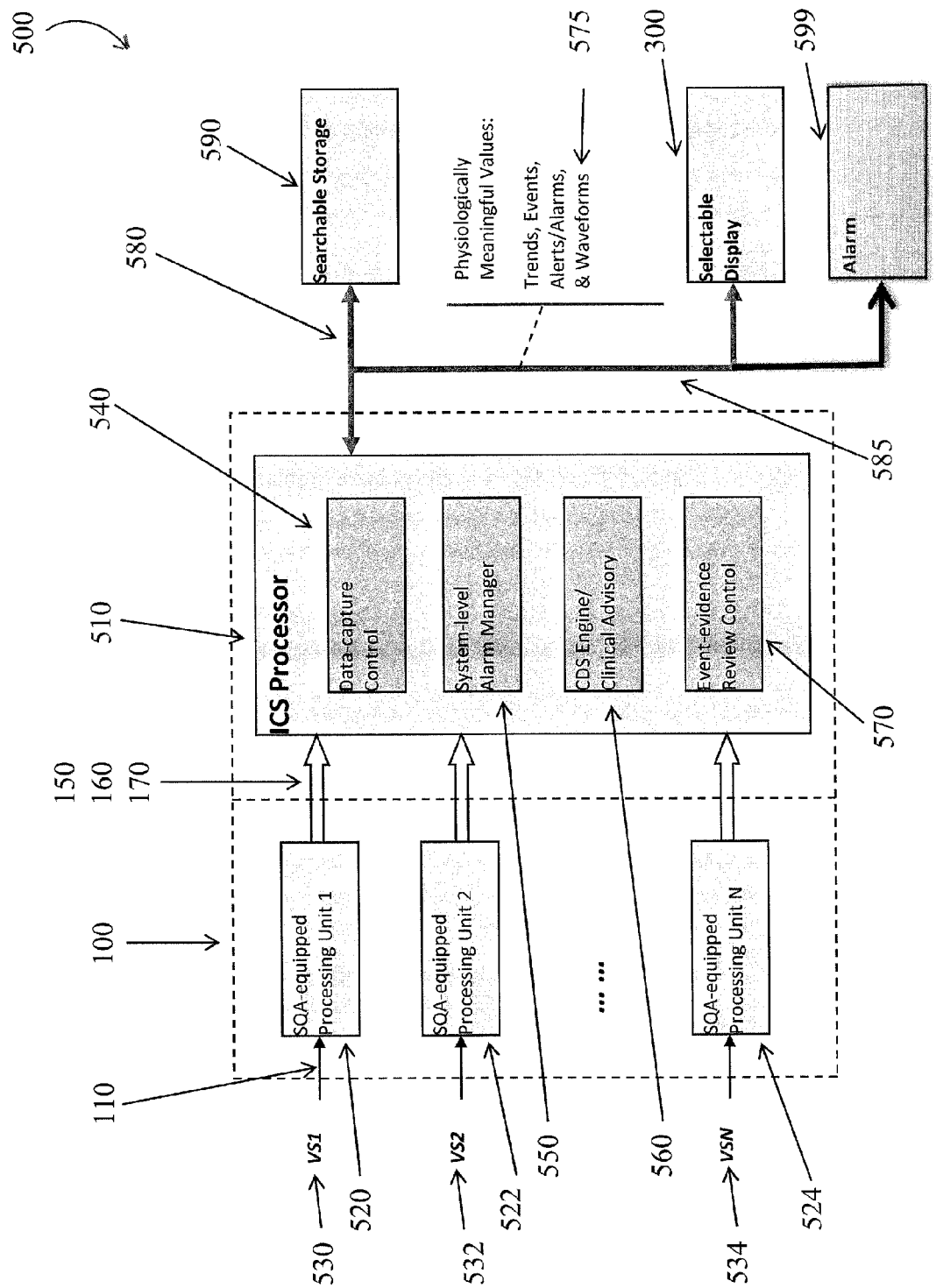

FIG. 5 illustrates the ICS processor layout.

Figure 6:
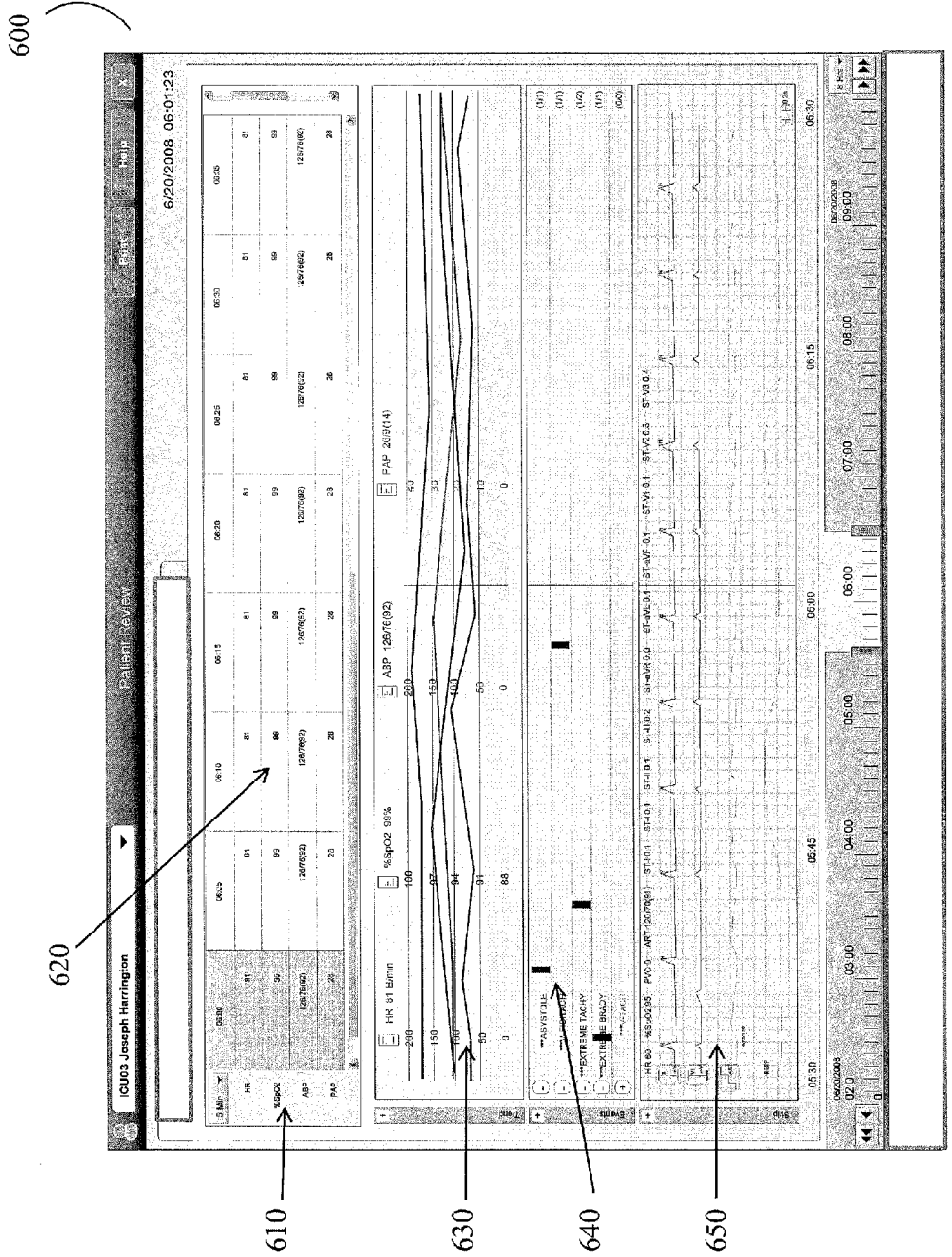

FIG. 6 illustrates a sample display.

Figure 7:
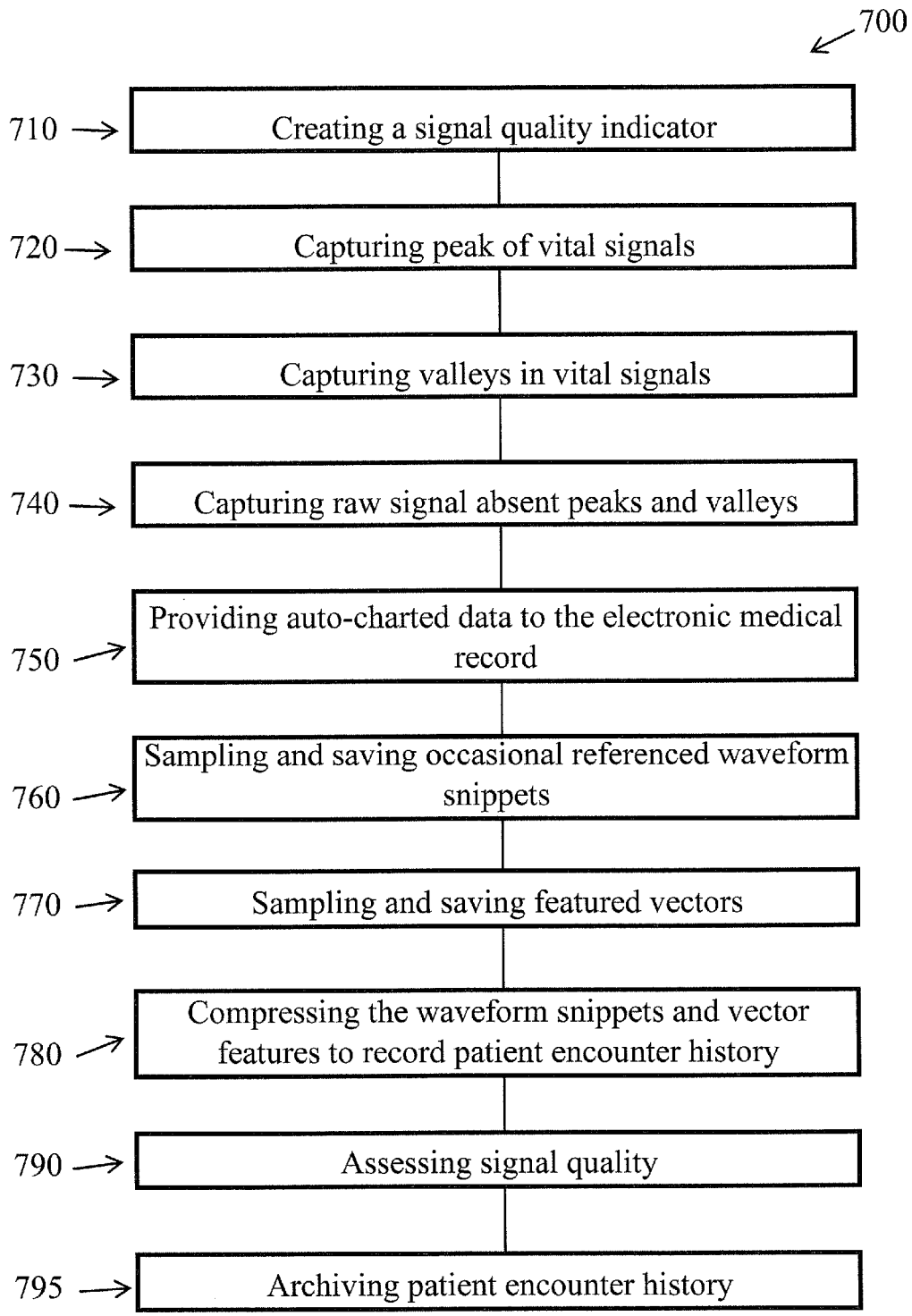

FIG. 7 illustrates a method flowchart.

Figure 1:
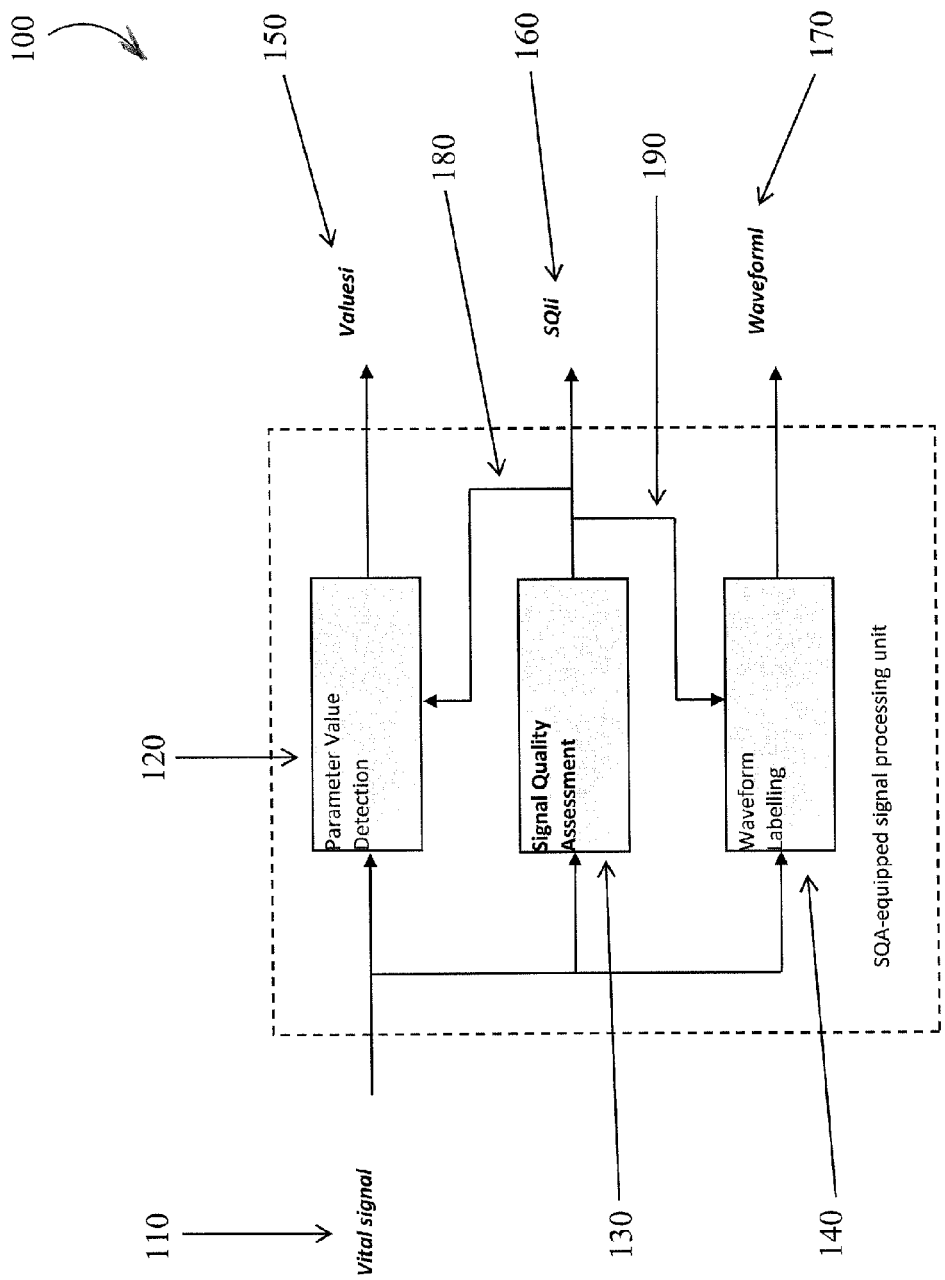
FIG. 1 is a diagrammatic illustration of a SQA-equipped vital-sign signal processing unit.

With reference to FIG. 1, in an automated SQA and control signal processing unit 100, a vital signal 110 is presented to a plurality of vital-sign signal processing units 120, 130, 140. A signal quality assessment processing unit (SQA) 130 assesses the incoming vital signal 110 for each of a plurality of episodes, such as beat-by-beat for cardiovascular signals, breath-by-breath for respiration, an appropriate time interval for temperature measurements, etc. The SQA components 130 generates a signal quality measure index ($SQI_i$) signal 160 for each episode, at each beat or cardiac cycle, for example, and indicates the quality of the signal corresponding to each episode. The $SQI_i$ is also passed 180, 190 to the other signal processing units 120, 140.

Figure 2:
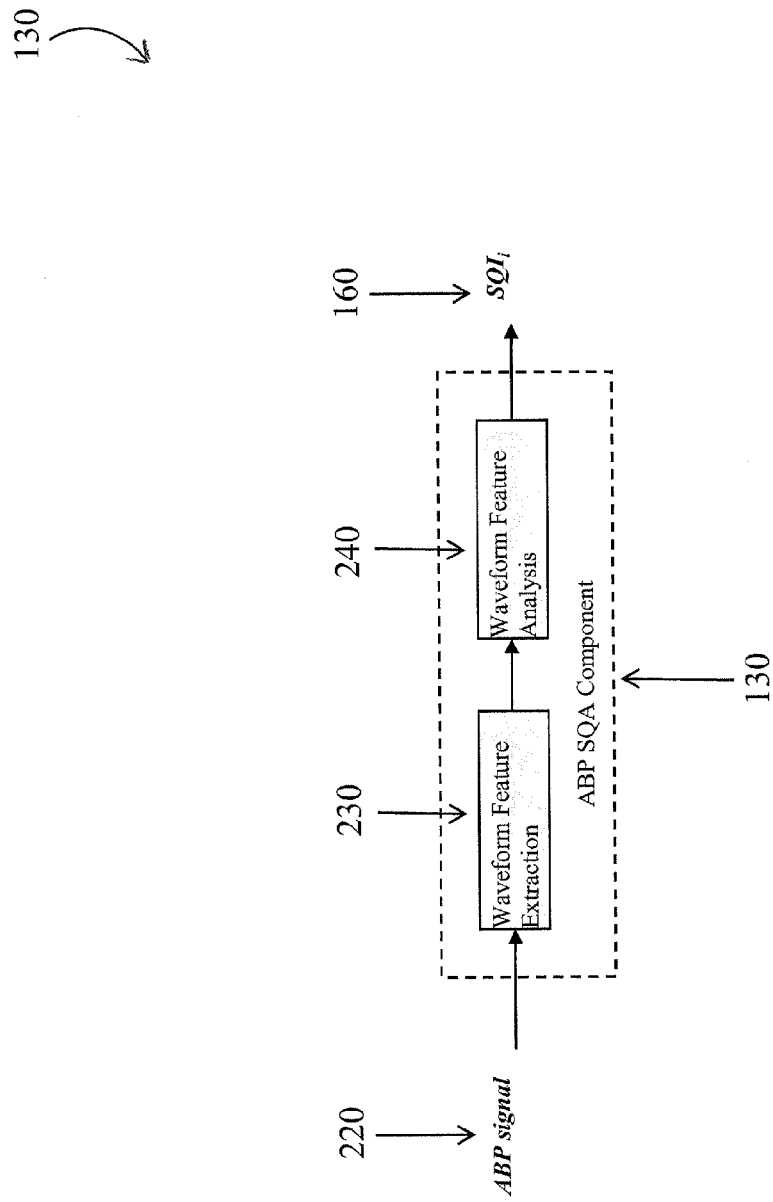
FIG. 2 is a diagrammatic illustration of an arterial blood pressure (ABP) signal quality assessment component.

The $SQI_i$ signals 160 are utilized by a parameter value detection (PVD) process in unit 120. The PVD processing unit 120 detects the vital sign parameter 110 values from the signal episodes that are rated as having good signal quality according to the $SQI_i$ and removes or replaces those rated as having poor signal quality according to the $SQI_i$. When no good SQI values (160) occur for an established period of time, the information control processor (510) indicates the SQI value (160) as bad and the vital value as questionable. A waveform labeling unit 140 attaches the $SQI_i$ to the signal waveform 110 to create an SQA-labeled waveform 170. In this manner, each episode of the waveform is labeled with a corresponding signal quality index value 160. Due to the signal processing unit 100, the reliability of the vital signal, e.g. free from noise and artifacts, is indicated by $SQI_i$. The resulting vital sign values are much more physiologically meaningful. The signal quality index value ($SQI_i$) signal 160, parameter values measured with SQI control ($Values_i$) 150, and $SQI_i$ labelled waveforms ($Waveform_i$) 170 are all available to the patient monitoring system or CIS. The true patterns of the vital sign changes are readily retrievable. Furthermore, since only the "true and meaningful" data are stored through this application and unnecessary data is not stored, fewer electronic, computer memory, database facilities, and hard copy resources are needed to store or represent the data related to the patient's visit to a medical facility With reference to FIG. 2, an example of implementing such a SQA component for an arterial blood pressure (ABP) signal 220 is presented. The ABP SQA component 130 includes an ABP waveform feature extraction (WFE) unit 230 and waveform feature analysis (WFA) unit 240 which produces the $SQI_i$ signal 160.

In the WFE process 230, a set of ABP waveform features are extracted on an episode by episode, e.g. beat by beat, basis. Those features are predefined to be sensitive for distinguishing between ABP signal 220 and artifacts. Such features may include amplitudes, which is the height of the peak of the signal above the center of the waveform or the depth of the valley of the signal below the center of the waveform. Features may also include slopes of how fast the peak rises above the center or how fast the valley falls below the center of the waveform. Features may also include a length of specific time intervals, such as how long the signal remains at a peak or a valley value. In the WFA unit 240, linguistic or fuzzy variables such as 'ABP_amplitude_is_too_large', 'ABP_keeps_rising_too_long', and 'ABP_slope_is_too_small' are employed to represent the waveform feature patterns, and a fuzzy logic reasoning approach is utilized to derive a signal quality index from inference of the linguistic variables.

An example of a fuzzy variable called 'ABP_signal_quality_is_good' is set forth below:

IF  ['ABP_amplitude_is_normal' (AN)]  AND
    ['ABP_slope_is_normal' (SN)]  AND
    [NOT 'ABP_keeps_rising_too_long' (KRTL)]  AND
    [NOT 'ABP_stays_high_too_long' (SHTL)]  AND
    [NOT 'ABP_with_blooked_transducer' (WBT)]
THEN 'ABP_signal_quality_is_good' (SQG)
    $SQI_i = \mu_{SQG} = \mu_{AN} \hat{} \mu_{SN} \hat{} (1 - \mu_{KRTL}) \hat{} (1 - \mu_{SHTL}) \hat{} (1 - \mu_{WBT})$ The signal quality index ($SQI_i$) 160 is defined as the value of the membership function of 'ABP_signal_quality_is_good'. As the WFE unit 230 and the WFA unit 240 processes proceed, an $SQI_i$ time series is generated which are corresponding to each beat cycle. Each of the $SQI_i$ has a value between zero, with 0 indicating the worst signal quality, to one with 1 indicating the best signal quality.

With reference to FIG. 3, an example of ABP signal quality index 160 is presented. A readout display 300 illustrates a trace resulting from above ABP SQA process. A top trace 310 represents an electrocardiogram (ECG) signal, a second trace 320 represents the ABP signal 220 with artifacts, and a bottom trace 330 represents the $SQI_i$, time series 160 generated by the ABP SQA unit 240 (Please note, in FIG. 3, the $SQI_i$ signal lags ABP by one beat interval). As illustrated, the $SQI_i$ indicates when the ABP signal quality is reliable and when it is artifacted or otherwise unreliable.

The system also enables the user of such a system to adjust the "tolerance" of an SQI to allow saving/capturing data at a desired data rate as well as signal quality. For example, if a user wants to store data at 5 minute resolution, the SQI can be adjusted accordingly to allow such a resolution of data to be stored.

With reference to FIG. 4A, the effect of signal quality assessment is presented. The ABP value can be selectively measured from the durations when the $SQI_i$, signal 170 indicates a reliable blood pressure measurement episode. A systolic ABP 410 without the signal quality assessment and control is shown in FIG. 4A and systolic ABP 440 measured from the same patient incorporating the signal quality control is shown in FIG. 4B.

In FIG. 4A, without signal quality assessment and control 410, the blood pressure signal 220 is plotted as a graph with time on an x-axis 412 and systolic ABP on a y-axis 414. The waveform is centered 415 around a value of 100 with extreme peaks 424, and double peaks 426, and lesser peaks 420, 422. The waveform also contains extreme valleys 434, and double valleys 436, along with less varying, lesser valleys 430, 432. The extreme peaks 424, 426 and extreme valleys 434, 436 may be caused by noise or signal distortion that may over ride and overwhelm the true peaks 420, 422 and the true valleys 430, 432 of the waveform.

In FIG. 4B after the application of signal quality assessment and control 440, the waveform is illustrated as a graph with an x-axis 442 and systolic ABP on a y-axis 444. The waveform is still centered 445 around the same value of 100 in this case, but the extreme peaks and valleys have been removed, leaving the more moderate peaks 450, 452, and moderate valleys 460, 462 remaining to indicate an artifact free clearer signal from which a trend of the blood pressure over time can be readily assured.

The charts demonstrate that processing the waveform signal by application of the signal quality assessment and control 100 produces a chart that contains much more physiologically meaningful ABP trend data especially, in terms of peaks and valleys than does the not processed waveform 410. The $SQI_i$ are attached to the signal on a beat-by-beat manner. So that by searching on $SQI_i$, it is easy to find where the signal is good and where is not. The reliability of alarms based on the vital sign values measured with signal quality control are therefore significantly improved.

With reference to FIG. 5, a patient monitoring Information Central Station (ICS) 500 incorporates the SQA-equipped Processing and control units 100 of FIG. 1. Although this processing is being described as being within the ICS, it could equally well be located within any device on the hospital network, including the bedside monitor. The ICS processor receives the outputs 150, 160, 170 from one, or a plurality of the SQA-equipped vital sign processing units (SQAe-PUs) 520, 522, 524. If a SQAe-PU is not available in the front-end device, then the raw vital signals ($VS_i$) 110 or a plurality of raw vital signals 530, 532, 534, may be received by the corresponding SQAe-PU functions at the ICS environment. An ICS processor 510 has the following processing components: data-capture control (DCC) 540; system-level alarm manager unit 550; a clinical decision support (CDS) engine or clinical advisory unit 560, and an event-evidence review control unit 570.

The DCC unit 540 determines how to capture the physiological meaningful vital sign values. For each vital sign channel, in a scheduled time interval such as 30 minutes, the DCC checks the $SQI_i$ value generated from the corresponding SQAe-PU at the scheduled times. If the $SQI_i$ value is sufficiently high, the value is captured. However, if the $SQI_i$ is poor at the scheduled time, then the value is not captured, and instead, the most recent value with good $SQI_i$ is located and captured. This is referred to as retrospectively correcting the data. Furthermore, the peaks 450, 452 and the valleys 460, 462 of the value with good $SQI_i$ are also captured. The data may include such matter 599 as physiologically meaningful values 575 as: trends, events, alerts, alarms, waveforms, and the like. A duration and sampling time of each waveform snippet that is stored can be a function of a use model. For example, for auto-charting data at one numeric sample per hour, 10 seconds or more of waveform data can be stored as part of the electronic medical record if the signal quality is deemed to be adequate. The user may also adjust the frequency and length that waveform data is stored based upon storage requirements or the like.

The system stores the captured vital sign data values and the corresponding $SQI_i$ and $SQI_i$ labeled waveforms 580 in an indexed searchable storage database 590 of patient records. The data is stored in a data warehouse arrangement to facilitate data analysis, such as cross correlation analysis, data mining for pattern detection within the accumulated data, projection and probability analysis in order to implement and operate a clinical decision support engine, and the like. The data and the data analysis components may produce output that may be displayed 585 in the readout display 300, such as but not limited to an LCD display, a cathode ray tube terminal, a waveform monitor, an LED display, and the like.

The system-level alarm manager 550 receives the captured vital sign values from above the described DCC unit 540, and performs validations of alarms that are issued from front-end devices or generates new alarms according to the alarm-criteria, as defined in the ICS, and/or based on the cross-correlations between different vital signs. Because the values that trigger the alarm are derived from clean signals, with good quality, the alarm performance is significantly improved. The validated and/or newly-generated alarms are also stored in the searchable storage 590 database and can be issued via an alarm interface 599.

The CDS engine/clinical advisory 560 receives the captured vital sign values from above DCC process unit, and performs various CDS applications which generate comprehensive clinical alerts and/or advisories about the patient state. As the input data values are more reliable than those from traditional manner, without signal quality control, the effectiveness of the CDS applications is significantly enhanced. The clinical alerts and/or advisories generated are also stored in the searchable storage database 590.

The event-evidence review control unit 570 provides comprehensive graphic user interface to the end users such as clinicians. It displays, in arbitrary scales, the captured vital sign and accompanying $SQI_i$ values, trends, the corresponding $SQI_i$ labeled waveforms and the like. The alarms/alerts are visualized and reviewed with underneath evidence at a desired scale and manner in a graphic image, text table, and the like. It also provides comprehensive search capability that allows clinicians to efficiently locate points of interests and/or specific statistics.

With reference to FIG. 6, the display 300, illustrates vital sign parameters 610 and their values at different time points 620, vital sign graphical trends 630, events 640, and associated captured waveform snippets 650. A user interface allows a clinician to rapidly review the high quality auto charted data to observe key events that may have been missed when they actually occurred. The interface may also be viewable across a computer operable network such as, but not limited to, a LAN, a WAN, and the Internet. The use of a network may also allow practitioners from remote locations to read, interact with, and adjust the readings displayed by the present application.

One utility of the present application is to provide high quality auto charted electronic medical records thus removing the need for user validation of data and providing improved accuracy. The $SQI_i$ is attached to the signal on an episode basis so that by searching on $SQI_i$, it is easy to find where the signal is good. The accuracy of alarms based on the vital sign values measured with signal quality control is therefore significantly improved.

With reference to FIG. 7, the steps of the method 700 are presented. In a first step 710, a signal quality indicator is created. In a peak capture step 720 true physiological peaks of vital signals are captured by utilizing the signal quality indicator. In a valley capturing step 730; true physiological valleys in vital signals are captured by utilizing the signal quality indicator. In a raw signal capturing step 740, a raw signal absent noisy peaks and noisy valleys and noisy signals is created. An auto-charted data step 750 provides physiologically meaningful, reliable auto-charted data to the electronic medical record searchable storage database 590. A snippet step 760 samples and saves physiologically meaningful, reliable waveform snippets periodically. A featured vector step 770 samples and saves physiologically meaningful, reliable feature vectors. A compressing step 780 compresses waveform snippets and vector features for recording in a patient encounter history. A quality step 790 addresses and saves signal quality indicators. An archiving step 795 archives patient encounter history. The method may also display the archived data.

The present application has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. A signal quality assessment and control system for capturing and archiving monitored physiological data, the system comprising:
a parameter value detection processing unit which receives physiological parameter signals and extracts a plurality of episodes of at least one physiological cycle in duration from the physiological parameter waveform signal;
a signal quality assessment processing unit which receives the physiological signals, accesses quality of each of the waveform episodes of the physiological signals, extracts waveform features of the waveform episodes, and generates a signal quality index indicative of the assessed quality of the physiological signals of each waveform episode based on the extracted waveform features; and
a waveform labeling unit which associates the signal quality index with each waveform episode of the physiological signals.

2. The systems according to claim 1, wherein the received physiological parameter signals of a continuously measured vital sign and the generating of the assessed quality index includes a comparison of the extracted waveform features of each episode with normal features of the vital sign measured.

3. The system according to claim 1, wherein the signal quality assessment processing unit includes:
a waveform feature analysis unit, which compares features of each episode with preselected characteristics of a vital sign measured by the physiological signal.

4. The system according to claim 3, wherein the waveform feature analysis unit determines whether each episode meets the preselected characteristics and further including at least one of:
a memory which stores the physiological parameter data of the episodes which meet the preselected criteria; and
a display which displays the physiological parameter data of the episodes which meet the preselected criteria.

5. The system according to claim 3 wherein the waveform feature analysis unit determines a signal quality index (SQI) and further including at least one of:
a display which concurrently displays the physiological parameter data of each episode and the corresponding signal quality index;
a memory which stores the physiological parameters data of each episode in association with its signal quality index; and
a tolerance which allows capturing the physiological parameters data at a desired rate.

6. The system according to claim 3, wherein the preselected characteristics include signal amplitude and rate of signal amplitude change.

7. The system according to claim 3, wherein the physiological parameter signals include an EKG signal and each episode corresponds to a cardiac cycle.

8. A patient monitoring station comprising:
a plurality of the signal quality and assessment systems according to claim 1;
an information control processor which receives the physiological parameter data and the signal quality signals from the systems and at least one of archives the received physiological parameters and the signal quality indices in a memory, displays on a display the received physiological parameters and the signal quality indices, or triggers an alarm.

9. The system according to claim 8, wherein the information control processor contains a data-capture control (DCC) which stores the episode of physiological parameter signal for an acceptable generated signal quality index and stores a most recent episode for an unacceptable generated signal quality index.

10. The system according to claim 1, wherein the generated signal quality index compares amplitude, slope, and length of time between extracted features of each episode.

11. The system according to claim 9, wherein the information control processor (ICP) contains at least one of:
a system-level alarm manager which generates an alarm based on a cross correlation between different vital signs measured by the physiological parameters of a patient;
a clinical decision support (CDS) engine/clinical advisory which includes at least one of a clinical alert and advisory about the patient's state generated from vital signs measured by the physiological signals received from the DCC; and an event-evidence review which controls a display using arbitrary scales at least one of: captured vital sign values, SQI values, trends, and corresponding SQI labeled waveforms.

12. A signal quality assessment and control method for capturing and archiving monitored physiological data, the method comprising:
- receiving physiological parameter waveform signals of a vital sign including a plurality of waveform episodes, each waveform episode having a duration of one or more physiological cycles;
- extracting features corresponding to each waveform episode, and generating signal quality index indicative of an assessed quality of the corresponding waveform episode based on the extracted features of the corresponding waveform episode; and
- associating each signal quality index with the corresponding waveform episode.

13. The method according to claim 12, further including:
- comparing each waveform episode with normal waveforms for the vital sign measured; and
- storing waveform episodes which are within a selected threshold of the normal waveforms based on the comparing.

14. The method according to claim 12, further including:
- determining physiological parameter trends based only on the waveform episodes corresponding to a signal quality index better than a signal quality index value.

15. The method according to claim 12, further including:
- determining whether each waveform episode meets preselected characteristics of a vital sign measured by the physiological signal;
- storing the physiological parameter data of the waveform episodes which meet the preselected characteristics; and
- displaying the waveform episodes of the physiological parameter signals which meet the preselected characteristics.

16. The method according to claim 14, wherein the preselected characteristics include a signal amplitude and a rate of signal change.

17. The method according to claim 14, wherein the physiological parameter signals include a blood pressure signal and each waveform episode corresponds to the physiological parameter waveform signals in an interval between blood pressure measurements.

18. The method according to claim 12, further including:
- capturing a peak, a valley, and the physiological parameter waveform signals;
- generating physiological parameter data through a parameter value detection processing unit to provide auto-charted data to an electronic record, by sampling and saving occasional waveform snippets;
- sample and saving featured vectors;
- compressing the waveform snippets and vector features to generate patient encounter recovery record; and
- compressing the waveform snippets and vector features to generate patient encounter recovery record.

19. The method according to claim 14, further including:
- generating an alarm based on a cross-correlation between the waveform episodes whose signal quality index exceeds a threshold.

20. A signal quality assessment and control method for capturing and archiving monitored physiological data, the method comprising:
- generating physiological meaningful and reliable parameter data from received physiological parameter signals received as raw waveforms;
- assessing a quality of the physiological parameter signals and generating signal quality indices indicative of the assessed quality of the physiological parameter signal;
- associating each signal quality index with corresponding physiological parameter data; and
- compressing and recording raw waveform snippets based on the signal quality indices thereby to compress and record the vital sign history of a patient encounter.

* * * * *